United States Patent [19]
Gehrung et al.

[11] Patent Number: 4,798,458
[45] Date of Patent: Jan. 17, 1989

[54] ANOMALOSCOPE

[75] Inventors: Hartmut Gehrung, Ostfildern; Hermanm Krastel, Neckargemuend; Rainer Kirchhuebel, Wetzlar, all of Fed. Rep. of Germany

[73] Assignee: Oculus Optikgeraete GmbH, Dutenhofen, Fed. Rep. of Germany

[21] Appl. No.: 860,637

[22] Filed: May 7, 1986

[30] Foreign Application Priority Data

May 7, 1985 [DE] Fed. Rep. of Germany ....... 3516285

[51] Int. Cl.$^4$ .............................................. A61B 3/06
[52] U.S. Cl. .................................... 351/242; 351/243
[58] Field of Search ........................ 351/242, 243, 237

[56] References Cited

U.S. PATENT DOCUMENTS 3,801,188  4/1974  Hunt et al. ......................... 351/243
3,947,099  3/1976  Grohlman et al. ................. 351/242

FOREIGN PATENT DOCUMENTS 7419060.6  6/1974  Fed. Rep. of Germany .
3209455    9/1983  Fed. Rep. of Germany .

OTHER PUBLICATIONS

J. H. Shaxby "A Simple Form of The Nagel Anomaloscope", Journal of Scientific Instruments, vol. 22, Jan. 1943, pp. 15 & 16.
Konstruktionsvorschlaege fuer ein modernes Anomaloskop (Design Proposals for a New Anomaloscope), Klin. Mbl. Augenheilk. 181 (1982), pp. 290–293, by W. D. Bockelmann.a
German Standard DIN Norm 6160 and an English translation thereof.

*Primary Examiner*—Rodney B. Bovernick
*Assistant Examiner*—Jay Ryan
*Attorney, Agent, or Firm*—Flynn, Thiel, Boutell & Tanis

[57] ABSTRACT

An anomaloscope for testing the human color sense which includes an optical device for producing a stimulus field including a red/green light mix and light of a yellow spectral color, a device for the mixing of the spectral colors green and red by apportioning them, such that upon strengthening one of them, the respective other one is reduced correspondingly. The anomaloscope further includes intensity control and indicating means for the spectral colors as well as for the portions of green and red determining the anomal quotient. For mixing the red and yellow spectral colors and for creating the stimulus field with a red/green light mix and a field of yellow spectral color, there is provided a partially translucent beam-splitting device arranged at approximately 45° relative to the optical axis of the anomaloscope. The first spectral color yellow and the second spectral color (green or red) illuminates from one side the beam-splitter plane approximately parallel to the optical axis. The third spectral color (red or green) illuminates the beam-splitter plane from the other side in the same area as the second spectral color. The path of rays of the third spectral color strikes the beam-splitter plane perpendicularly relative to the path of rays of the second spectral color.

16 Claims, 1 Drawing Sheet

ANOMALOSCOPE

FIELD OF THE INVENTION

The invention relates to an anomaloscope for testing the human color sense, comprising an optical device for producing a stimulus field with a field having a red/-green and a yellow spectral color, a device for the mixing of the spectral colors green and red such that upon a strengthening of a spectral color, the respectively other one is suitably reduced, and comprising indicating means for indicating the intensity of the spectral colors and for the parts of the green and red spectral colors for determining the anomal quotient.

BACKGROUND OF THE INVENTION

Testing the human color sense has meaning in the field of medicine for humans who work in certain areas of traffic or techniques wherein a recognizing of colored optical signals is important. The capability of testing the color-differentiating capability of humans is in practice particularly important in the red-green range.

The tests of the human color sense are today carried out mostly by pigment samples (for example, so called pseudoisochromatic tables), with transparent color filter glasses (color test plate) or by mixing and comparing spectral lights with the anomaloscope according to Nagel.

The anomaloscope of Nagel determines the capability of seeing colors in relationship to the seeing of red-green. The determination is made by comparing a binary mixture of a red and a green spectral light with a monochromatic yellow. From the mixture ratio and the adjusted luminous density of the comparison yellow, it is possible to recognize the color emmetropia of the person being tested with respect to seeing red-green. The anomaloscope according to Nagel has a mechanically very expensive construction. The red-green mixture is effected by two parallel inlet gaps, the outer gap jaws of which are nonchangeably fixed and are adjusted to the red or green wave length. The inner edges of the gap are formed by a common gap jaw which is movable by means of a fine adjustment screw. By moving the fine adjustment screw, the one gap is enlarged by the same amount as the other one is restricted and thus the mixture ratio of the two spectral lights can be varied. Next to the two mixing gaps there is arranged a third, unilateral gap for the comparison light, which is adjusted to the yellow color and by means of a movable gap jaw opens the yellow gap toward the long-wavelength side. The screws for adjusting the gap have scales. When the gap is closed, the scale shows 0 and when the gap is fully open the value 87. The usable width for the two mixing gaps is 73 intervals. In the position 0 the red gap is closed and the green gap is fully open, while in the position 73 the green gap is closed and the red gap is fully open. The produced light extends through a complicated optic into the eye of the viewer, so that the viewer sees in the lower half of the field of vision the homogeneous yellow and in the upper half, depending on the position of the mixing gap, a homogeneous red or a green spectral light or a mixture of the lights. The setting on the anomaloscope and its adjustment occurs according to the DIN norm 6160. However, an anomaloscope according to Nagel is decidedly complicated and expensive.

It also has already been suggested to use luminescence diodes for color tests, whereby two diodes of the same color are used, the brightnesses of which are modulated. If one modulates the lights of the wave lengths of the two luminescence diodes in opposite directions, that is, if one permits the one to light up, while the other one goes dark, and vice versa, then the intensity of the lights must be chosen accordingly, so that the one, who does not recognize anything in this spectral range, does no longer recognize a shimmer. However, the field of use is very limited, since a differentiating between anomaly and anopy cannot be determined with the method. Moreover, the device does not permit the common differentiation according to the Rayleigh equation, that is the determining of the anomal quotient.

The methods of testing with pigment samples and color filter glasses a high inexactness and thus not always usable results.

From Offenlegungsschrift No. 32 09 455 it is furthermore known to use two luminescence diodes for a device of the quantitative testing of the color sense and its disorders, whereby one luminescence diode emits a yellow light and the second luminescence diode is a so called two-color luminescence diode, which emits both a red and also a green light. By mixing the red and the green, substantially monochromatic, light sources it is possible to simulate the color frequencies in the red-green range. In the practical design of such a device, the two luminous diodes are arranged relatively close to one another, such that the person being tested must judge these two luminous diodes with respect to their color characteristic and brightness. Experience has shown that the measured values obtained with such a device cannot be compared with the standardized values which are fixed in the norm.

The basic purpose of the invention is to provide an anomaloscope of the abovementioned type such that the same permits a standard testing corresponding with the anomaloscope of Nagel. In comparison to the known anomaloscope, our design is substantially simpler and thus less expensive to manufacture and offers the possibility of providing the person being tested a neutralizing white stimulus field between the individual measurements.

The inventively constructed anomaloscope for testing the human color sense has a partially translucent mirror arranged in the optical axis of a beam-splitting cube, the beam-splitting cube has the advantage that an equality of the optical light paths exists, while in the case of the partially translucent mirror, the paths of the rays are optically not equal. The portion of the rays which has been let through, extends through an additional path of glass, experiencing a parallel shifting. Opposite this disadvantage stands the fact that it can be manufactured less expensively. A beam-splitter plane of a splitting mirror of the beam-splitting cube is arranged approximately 45° with respect to the optical axis. To produce the monochromatic yellow, green and red light, single-color luminescence diodes are preferably used. A single-color luminescence diode emits a light, the spectral range of which includes a relatively narrow band range. In order to obtain a still more narrow spectral range, it is preferable to arrange one or several band-stop filters in front of each luminescence diode.

It is also conceivable to use halide lamps in place of the luminous diodes. Interference filters are arranged before the halide lamps. Of course, the interference filters are significantly more expensive and show the disadvantage that these are not permanently constant.

To create the anomaloscope, two of the light sources are arranged parallel to the optical axis, such that the two light sources have the same opposite distance from the optical axis. A partition wall preferably arranged between these two light sources, so that they do not interfere with one another. A third light source is arranged perpendicularly to the two light sources, which third light source illuminates the same area of the beam splitter plane that is illuminated by the second light source, namely, the one wherein the colors are mixed. By using the splitting mirror of the beam-splitting cube, a mixing of the spectral colors and a mixing of the strengthening of one spectral color with a weakening of the corresponding other spectral color is facilitated in a relatively simple manner. The anomaloscope, according to the invention, offers in a simple manner a co-observing possibility, so that the rays exiting from the free side of the beam splitter plane can be observed, which rays are moved, if necessary, with the help of a surface mirror into a position suitable for the co-observer.

A further splitting mirror is preferably inserted into the optical axis of the anomaloscope, which mirror is arranged at 45° with respect to the optical axis and through which a white stimulus field is blended in. The norm for carrying out the tests states that this white stimulus field must always be added after a test. The actual view provided for testing absolute adjustment width is seen by the person being tested for only about 2 to 3 seconds, while for determining relative adjustment width, a respective test view or field must be viewed up to a maximum of 15 seconds. Since the white stimulus field is to be viewed only for a relatively short time, and since a subsequent illuminating by a halide lamp, commonly used, is to be avoided, a shutter is arranged, according to the invention, behind the halide lamp for releasing the rays only for a predetermined time. The luminous diodes are turned off during this time. If further halide lamps are used for the production of the yellow, green and red spectral colors, further apertures are arranged in front of the lamps.

Further advantageous developments of the invention will become apparent from a review of the following description and with reference to the accompanying drawings.

BRIEF DESCRIPTION OF THE DRAWINGS

One exemplary embodiment of the invention will be described in greater detail hereinafter in connection with the drawing, in which.

DETAILED DESCRIPTION

Figure 1:
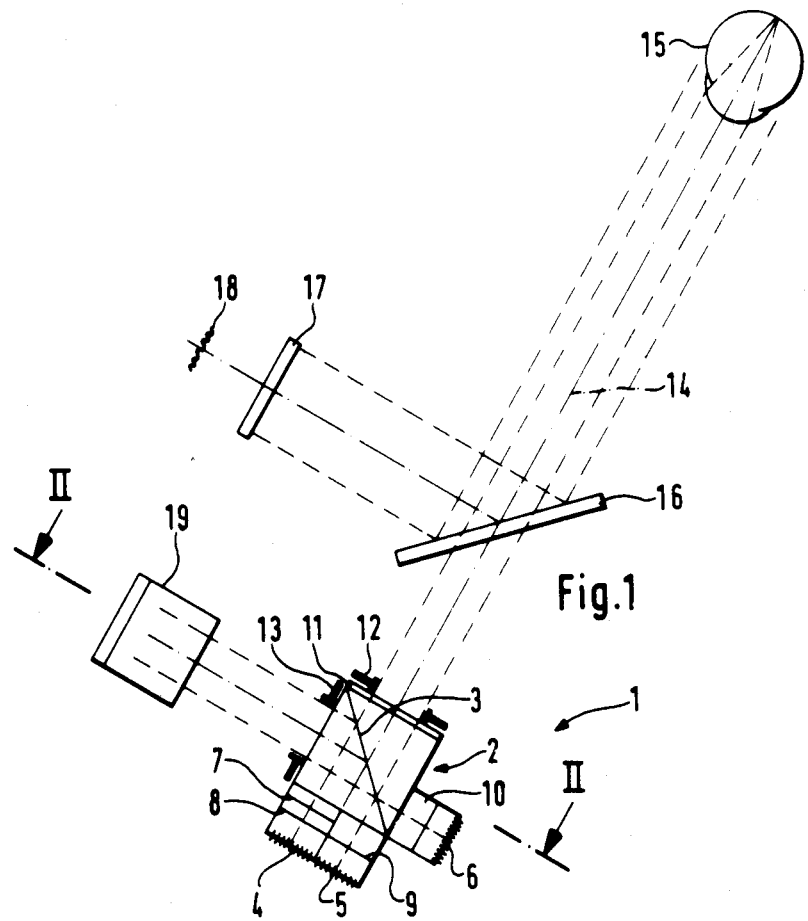
FIG. 1 is a top view of an inventively constructed anomaloscope.
Figure 2:
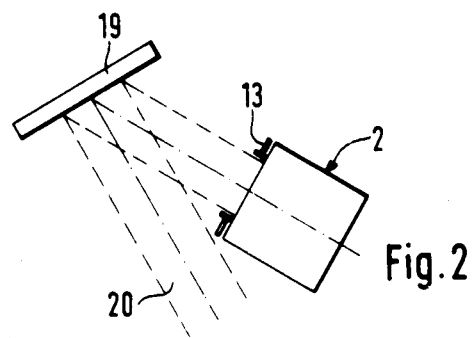
FIG. 2 is a cross-sectional view taken along the line II—II of FIG. 1.

The anomaloscope 1 illustrated in FIG. 1 consists of a beam-splitting cube 2, the beam-splitting plane 3 of which is arranged at a 45° angle with respect to the optical axis 14 of the anomaloscope 1. The eye of the person being tested, who looks into the anomaloscope 1 which is arranged in a housing (not illustrated) is identified by the reference numeral 15.

Two luminescence diodes 4,5 are arranged parallel with respect to the optical axis 14 of the anomaloscope 1. The luminescence diode 4 is the yellow primary valence diode. The luminescence diode 5 is the green primary valence diode. Both diodes are separated from one another, so that they do not influence one another.

Two filters 7,8 are arranged in front of the yellow luminescence diode 4, which filters together with the yellow luminescence diode result in a monochromatic light of 589 μm. A filter 9 is also arranged in front of the green luminescence diode 5, so that a wave length of 546 μm is obtained. A filter 10 is also arranged in front of a red luminescence diode 6, so that a wave length of 670 μm is obtained. The two luminescence diodes 4,5 are arranged at an equal distance from the optical axis 14 and have a path of rays which extend parallel with respect to the optical axis. The third luminescence diode is arranged perpendicularly with respect to the optical axis 14 and illuminates the beam-splitting plane 3 in the same area as the green luminescence diode 5, so that a mixture of the two beams is obtained. These mixed rays reach both the eye 15 of the person being tested and also a surface mirror 19, which is used to co-observe. The ray of the yellow luminescence diode also strikes the beam-splitting plane 3 and is divided into a ray that extends parallel to the optical axis 14 as well as perpendicular to same, such that the ray that extends perpendicular to the optical axis 14 strikes the surface mirror 19 and is used to co-observe. The path of the rays is so deflected by the surface mirror 19 that the co-observer can see the path of rays in a comfortable position.

A splitting mirror 16 is inserted into the optical axis 14, the mirror being arranged at 45° to the optical axis. The splitting mirror should have a high degree of transmission, so that the luminous intensity of the luminescence diode is not too strongly dampened. A halide lamp 18 is arranged perpendicularly offset from the optical axis 14, a filter 17 being arranged in front of the lamp. The halide lamp receives with the help of the filter a color temperature of 6,770° Kelvin, so that the light of the halide lamp corresponds with the normal type of light C. The person being tested sees this light through the partially transmitting mirror which is inclined at 45° and which is mounted between his eye and the stimulus field of the anomaloscope. The mirror permits 80% of the rays of the light source of the color surface to pass and reflects 20% of the rays of the light source 18 for the brightness adaptation.

A test-field aperture 12 is arranged in front of the beam-splitting cube 2, which aperture creates the stimulus field in a standard size. Creating the mixture of the color light with the help of two luminescence diodes is preferred over the use of a two-color luminescence diode, since the individual primary valences can be defined more exactly than can be achieved with the help of filters arranged in front thereof.

The intensity control of the luminescence diodes occurs by pulse-width modulation. The change between on and off or between red and green is clearly above the flicker-fusion frequency of the human eye, for example above 100 Hertz. It is possible with the help of the anomaloscope to obtain a brightness control analogous to the Nagel anomaloscope. The more red or more green coloring of the mixture is determined red to green through the relationship of the pulse widths. A calculation to determine the anomal quotient is not needed, since the button for the red-green mixture shows to a scale which is calibrated corresponding with the anomaloscope of Nagel.

The person being tested should look into the anomaloscope monocularly through a dark tube. The viewing opening should be covered up with a plane parallel, dereflected small glass. Aside from light adaptation phases, the same lighting and the same adaptation condition exists in the tube as in the Nagel anomaloscope. The test image is seen at an angle of 2°, which is achieved by the length of the tube and the aperture of the field of vision 12. To achieve homogeneous stimulus fields, a ground-glass plate 11 is inserted behind the beam-splitting cube 2, which plate 11 balances the inhomogeneities in the luminescence diodes in the luminous field. However, it is also conceivable to arrange this ground-glass plate on the other side of the splitting mirror 16.

To summarize the foregoing, the anomaloscope 1 is used for testing the human color sense. It includes an optical device 2 for producing a stimulus field including a red/green light mix and light of a yellow spectral color and a device 3 for the mixing of the spectral colors green and red by apportioning them, such that upon strengthening one of them, the respective other one is reduced correspondingly, and an intensity control and indicating means for the spectral colors as well as for the portions of green and red determining anomal quotient values. The optical device 2 includes a partially translucent beam-splitter for mixing the red and yellow spectral colors and for creating the stimulus field with a red/green light mix and a field of yellow spectral color. The beam-splitter has a beam-splitter plane 3 arranged at approximately 45° relative to the optical axis 14 of the anomaloscope. The first spectral color yellow and the second spectral color (green or red) illuminates the beam-splitter plane 3 from one side approximately parallel to the optical axis 14. The third spectral color (red or green) illuminates the beam-splitter plane 3 from the other side in the same area as the second spectral color. The path of rays of the third spectral color strikes the beam-splitter plane 3 perpendicularly relative to the path of rays of the second spectral color.

An inventively constructed anomaloscope is distinguished by a simple design into which single-color luminescence diodes can be inserted, which in addition can be adjusted very exactly through band filters to the desired monochromatic radiation. By using a splitting mirror or a beam-splitting cube, a mixing of the light given off by the luminescence diodes is moreover achieved in a simple and reliable manner. Furthermore, values compatible with the Nagel anomaloscope are obtained, and, in addition, the advantage in view of the anomaloscope of Nagel exists such that, alternating with the colored stimulus image, a white stimulus image for neutralization can be added.

The embodiments of the invention in which an exclusive property or privilege is claimed are defined as follows:

1. In an anomaloscope for testing the human color sense, comprising an optical device for producing a stimulus field including a red/green light mix and light of a yellow spectral color, a device for the mixing of the spectral colors green and red by apportioning them, such that upon strengthening one of them, the respective other one is reduced correspondingly, and comprising intensity control and indicating means for the spectral colors as well as for the portions of green and red determining anomal quotient values, the improvement wherein for mixing the red and yellow spectral colors and for creating the stimulus field with a red/green light mix and a field of yellow spectral color, said optical device is provided with a partially translucent beam-splitting means having a beam-splitter plane arranged at approximately 45° relative to the optical axis of said anomaloscope, wherein the first spectral color yellow and the second spectral color (green or red) illuminates said beam-splitter plane from one side approximately parallel to the optical axis, wherein the third spectral color illuminates said beam-splitter plane from the other side in the same area as the second spectral color, and wherein the path of rays of the third spectral color strikes said beam-splitter plane perpendicularly relative to the path of rays of the second spectral color.

2. The anomaloscope according to claim 1, wherein the spectral colors are produced by a halide lamp, in front of which are arranged interference filters.

3. The anomaloscope according to claim 1, wherein single-color luminescence diodes are used as light sources for the yellow, red and green spectral colors serve, respectively, each luminescence diode having a narrow and differentiated spectral range.

4. The anomaloscope according to claim 3, wherein a light ground-glass is arranged in front of each diode for balancing the residual inhomogeneities of the diode-illuminated field.

5. The anomaloscope according to claim 3, wherein at least one band-stop filter is arranged in front of each luminescence diode.

6. The anomaloscope according to claim 1, wherein an aperture is arranged on the side of said beam-splitter plane which faces the eye of the patient.

7. The anomaloscope according to claim 6, wherein along the optical axis of said anomaloscope, a further beam-splitting means is inserted, the beam splitter plane of which is inclined at approximately 45° relative to the optical axis, and wherein white light is projected onto the beam-splitter plane perpendicularly relative to the optical axis.

8. The anomaloscope according to claim 7, wherein a halide lamp serves as a light source.

9. The anomaloscope according to claim 7, wherein a shutter is inserted into the path of rays between the light source and the beam-splitter plane.

10. The anomaloscope according to claim 7, wherein a ground-glass plate is inserted into the path of rays between the light source and said beam-splitter plane.

11. The anomaloscope according to claim 10, wherein a surface mirror is arranged on the side of said beam-splitter plane which is opposite the third spectral color.

12. The anomaloscope according to claim 11, wherein between said surface mirror and said beam-splitter plane there is inserted an aperture for defining the field of vision.

13. The anomaloscope according to claim 1, wherein said anomaloscope is arranged in a housing.

14. The anomaloscope according to claim 1, wherein said anomal quotient values obtained are converted to digital values which are indicated digitally.

15. The anomaloscope according to claim 1, wherein the intensity control means includes pulse-width modulation means and wherein the alternating frequency between turning on and off is definitely above the flicker-fusion limit of the human eye.

16. The anomaloscope according to claim 15, wherein the alternating frequency is approximately 100 Hertz.

* * * * *